United States Patent [19]
Cox

[11] Patent Number: 5,868,706
[45] Date of Patent: *Feb. 9, 1999

[54] CATHETER WITH REINFORCED OBLONG TRANSVERSE CROSS SECTION

[75] Inventor: Daniel L. Cox, Palo Alto, Calif.

[73] Assignee: Advanced Cardiovascular Systems, Inc., Santa Clara, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 820,052

[22] Filed: Mar. 17, 1997

Related U.S. Application Data

[63] Continuation of Ser. No. 364,608, Dec. 27, 1994, abandoned.

[51] Int. Cl.⁶ .................................................. A61M 29/00
[52] U.S. Cl. ............................ 604/96; 604/280; 604/282
[58] Field of Search ................................ 604/96, 99, 102, 604/103, 282, 281, 283, 284, 280; 606/191, 192, 194; 128/656–658; 600/433–435

[56] References Cited

U.S. PATENT DOCUMENTS

| | | | |
|---|---|---|---|
| 2,248,934 | 7/1941 | Auzin | 604/103 |
| 2,457,244 | 12/1948 | Lamson | 604/96 |
| 2,912,981 | 11/1959 | Keough | 604/98 |
| 2,930,377 | 2/1960 | Cowley | 128/344 |
| 3,112,478 | 11/1963 | Colburn | 128/350 R |
| 3,112,748 | 12/1963 | Colburn | 128/350 R |
| 3,769,981 | 11/1973 | McWhorter | 604/96 |
| 3,978,863 | 9/1976 | Fettel et al. | 606/192 |
| 3,983,879 | 10/1976 | Todd | 604/96 |
| 4,295,464 | 10/1981 | Sihata | 604/98 |
| 4,406,656 | 9/1983 | Hattler et al. | 604/43 |
| 4,458,677 | 7/1984 | McCorkle, Jr. | 128/786 |
| 4,484,579 | 11/1984 | Meno et al. | 606/194 |
| 4,553,959 | 11/1985 | Hickey et al. | 604/96 |
| 4,563,170 | 1/1986 | Aigner | 604/43 |
| 4,601,713 | 7/1986 | Fuqua | 604/96 |
| 4,723,936 | 2/1988 | Buchbinder et al. | 604/96 |
| 4,748,982 | 6/1988 | Horzewski et al. | 606/192 |
| 4,771,777 | 9/1988 | Horzewski et al. | 604/96 |
| 4,776,841 | 10/1988 | Catalano | 604/280 |
| 4,790,315 | 12/1988 | Mueller, Jr. et al. | 606/194 |
| 4,850,373 | 7/1989 | Zatloukal et al. | 604/44 |
| 4,877,031 | 10/1989 | Conway et al. | 604/96 |
| 4,892,519 | 1/1990 | Songer et al. | 604/96 |

(List continued on next page.)

FOREIGN PATENT DOCUMENTS

| | | |
|---|---|---|
| 0 197787 | 10/1986 | European Pat. Off. . |
| 197787 | 10/1986 | European Pat. Off. . |
| 0 277 368 | 8/1988 | European Pat. Off. . |
| 0 515 119 | 11/1992 | European Pat. Off. . |
| 3522782 A1 | 1/1987 | Germany . |
| 3742710 | 7/1998 | Germany . |
| WO/90 08567 | 8/1990 | WIPO . |
| WO/93 18813 | 9/1993 | WIPO . |
| 9411053 | 5/1994 | WIPO ...................................... 604/96 |
| WO-94 11053 | 5/1994 | WIPO . |

*Primary Examiner*—Wynn Wood Coggins
*Assistant Examiner*—Cris L. Rodriguez
*Attorney, Agent, or Firm*—Heller, Ehrman, White & McAuliffe

[57] ABSTRACT

An improved dilatation catheter is described which has an oblong transverse cross-section along essentially its entire length and a stiffening mandrel extending within the proximal section and a part of the distal portion. In a presently preferred embodiment, the large dimension of the proximal section of the catheter shaft is greater than the corresponding large dimension of the distal shaft section and a tapered region is provided between the proximal and distal shaft sections. The stiffening mandrel has a proximal section with at least one dimension greater than the corresponding dimension of the distal section and a tapered transition section is provided between the proximal and distal mandrel sections. The length of the proximal section of the mandrel is such so as to locate the tapered transition section of the mandrel within the proximal section of the catheter shaft. This results in a smoother overall transition between the proximal and distal sections of the catheter shaft.

15 Claims, 1 Drawing Sheet

U.S. PATENT DOCUMENTS

| | | | |
|---|---|---|---|
| 4,906,230 | 3/1990 | Maloney et al. | 604/95 |
| 4,917,666 | 4/1990 | Solar et al. | 604/96 |
| 4,943,278 | 7/1990 | Euteneuer et al. | 606/194 |
| 4,944,745 | 7/1990 | Sogard et al. | 604/103 |
| 4,973,278 | 11/1990 | Euteneuer et al. | 604/194 |
| 4,998,923 | 3/1991 | Samson et al. | 604/95 |
| 5,037,386 | 8/1991 | Marcus et al. | 604/43 |
| 5,040,548 | 8/1991 | Yock | 128/898 |
| 5,046,503 | 9/1991 | Schneiderman | 606/194 |
| 5,071,425 | 12/1991 | Gifford, III et al. | 606/159 |
| 5,102,390 | 4/1992 | Crittenden et al. | 606/194 |
| 5,106,368 | 4/1992 | Uldall et al. | 604/43 |
| 5,135,535 | 8/1992 | Kramer | 606/194 |
| 5,149,330 | 9/1992 | Brightbill | 604/280 |
| 5,154,725 | 10/1992 | Leopold | 606/194 |
| 5,156,594 | 10/1992 | Keith | 604/96 |
| 5,171,222 | 12/1992 | Euteneuer et al. | 604/102 |
| 5,176,637 | 1/1993 | Sagae | 604/96 |
| 5,195,971 | 3/1993 | Sirhan | 604/96 |
| 5,217,440 | 6/1993 | Frassica | 604/282 |
| 5,226,880 | 7/1993 | Martin | 604/99 |
| 5,242,396 | 9/1993 | Evard | 604/96 |
| 5,300,025 | 4/1994 | Wantiak | 604/96 |
| 5,334,148 | 8/1994 | Martin | 604/96 |
| 5,425,711 | 6/1995 | Ressemann et al. | 604/96 |
| 5,470,315 | 11/1995 | Adams | 604/96 |
| 5,507,768 | 4/1996 | Lau et al. | 606/198 |
| 5,531,690 | 7/1996 | Aular | 604/102 |
| 5,545,134 | 8/1996 | Hilaire et al. | 604/96 |
| 5,545,138 | 8/1996 | Fugso et al. | 604/102 |
| 5,549,556 | 8/1996 | Wdoude-Fay et al. | 604/102 |
| 5,611,775 | 3/1997 | Machold et al. | 604/53 |

U.S. Patent | Feb. 9, 1999 | 5,868,706
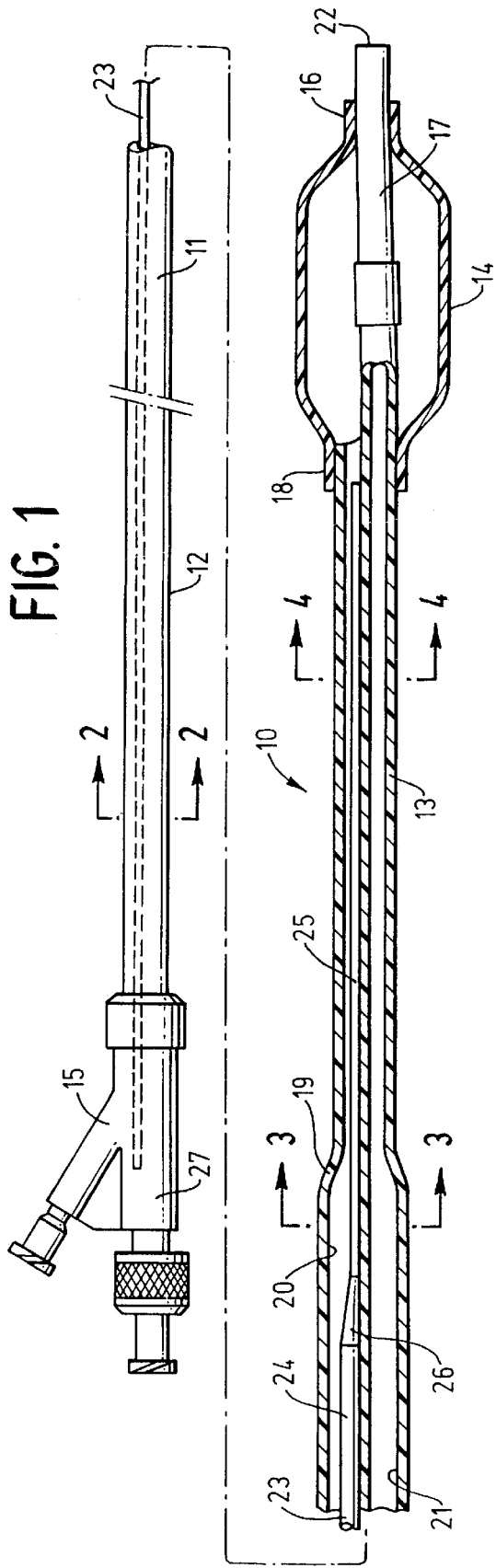

CATHETER WITH REINFORCED OBLONG TRANSVERSE CROSS SECTION

This is a continuation of application Ser. No. 08/364,608 which was filed on Dec. 27, 1994 now abandoned.

BACKGROUND OF THE INVENTION

This invention relates to the field of intravascular catheters and, more particularly, to a dilatation catheter for percutaneous transluminal coronary angioplasty (PTCA).

In PTCA procedures a guiding catheter having a preformed distal tip is percutaneously introduced into the patient's femoral artery by means of a conventional Seldinger technique and retrogradely advanced until the distal portion of the guiding catheter is located within the patient's ascending aorta with distal tip of the guiding catheter seated in the ostium of a desired coronary artery. The proximal end of the guiding catheter is torqued from outside the patient to guide distal tip of the guiding catheter into the desired ostium. A guidewire is positioned within an inner lumen of an dilatation catheter and then both are advanced through the guiding catheter to its distal end. The guidewire is first advanced out of the distal end of the guiding catheter into the patient's coronary artery until the distal end of the guidewire crosses a lesion to be dilated. Then the dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilation balloon is inflated with liquid one or more times to a predetermined size at relatively high pressures to expand the arterial passageway. Generally, the inflated diameter of the balloon is approximately the same diameter as the native diameter of the body lumen being dilated so as to complete the dilatation but not overexpand the healthy artery wall on either side of the stenosis. After the balloon is finally deflated, blood flow resumes through the dilated artery and the dilatation catheter can be removed therefrom.

Commercially available over-the-wire dilatation catheters for angioplasty and other vascular procedures usually comprise an elongated shaft with an inflatable dilatation member on a distal section of the shaft and an adapter on the proximal end of the shaft for the delivery of inflation fluid through an inner lumen extending through the catheter shaft to the interior of the inflatable dilatation member.

Over-the-wire dilatation catheters generally have relatively stiff proximal sections to provide pushability to the catheter shaft and relatively flexible distal sections to facilitate passing through tortuous coronary anatomy. The difference in mechanical property requirements between the proximal and distal sections of the catheter shaft usually requires the use of different materials, which in turn complicates the catheter manufacturing because the proximal and distal sections must be separately made and then secured together by heat or fusion bonding or a suitable adhesive. The difference in mechanical properties between the proximal and distal shaft sections also increases the difficulty in forming a smooth transition between the proximal and distal sections of the catheter shaft.

What has been needed is an easily manufactured dilatation catheter which has a relatively stiff proximal section for pushability, a very flexible distal section to facilitate advancement over a guidewire, i.e. trackability, within a patient's coronary anatomy and a smooth transition between the proximal and distal sections. The dilatation catheter of the present invention responds to these and other needs.

SUMMARY OF THE INVENTION

This invention is directed to a dilatation catheter for performing an angioplasty procedure which has an elongated shaft with an oblong transverse cross-sectional shape along a substantial portion of its length.

The portion of the catheter shaft with an oblong transverse cross-section extends along a substantial length of the catheter shaft and preferably at least from a location in the proximal section of the catheter shaft to a location in the distal section of the catheter shaft. The catheter has an inflation lumen extending from the proximal end of the shaft to a location in the distal shaft section of the catheter shaft proximal to the distal end and in fluid communication with an inflatable dilatation member on the distal shaft section, and a guidewire lumen extending therein to a port in the distal end of the shaft. The catheter shaft is provided with a stiffening or reinforcing mandrel, preferably within the inflation lumen, which extends within the portion of the catheter shaft having an oblong transverse cross-section. The mandrel may be disposed within the polymer material forming the catheter shaft and not within the inflation lumen. The stiffening mandrel preferably has a relatively stiff proximal section and a relatively flexible distal section. The length of the proximal section of the mandrel should be less than the length of the proximal section of the catheter shaft so that the junction between the relatively stiff proximal section of the mandrel and the relatively flexible distal section of the mandrel is located at least partially within the proximal shaft section of the catheter to provide a smooth transition between the proximal and distal sections of the catheter shaft. If the mandrel is made entirely of the same material, the proximal section should have larger transverse dimensions than the distal section and a tapered transition region should be provided between the proximal and distal sections. In a presently preferred embodiment, the proximal end of the mandrel is secured to an adapter mounted on the proximal end of the catheter shaft to fix the position within the catheter. The distal end of the mandrel is free, i.e. is not secured within the inflation lumen, and should be located at or proximal to the proximal end of the inflatable dilatation member. The mandrel may be provided with a plurality of sequential sections with traverse dimensions decreasing in the distal direction, preferably with tapered transition sections between the mandrel sections.

The portion of the catheter shaft which has an oblong transverse cross-sectional shape has a large transverse dimension about 1.1 to about 3 times, preferably about 1.2 to about 2.5 times, greater than a small transverse dimension perpendicular to the larger dimension. For dilatation catheters suitable for coronary arteries, the differential between the large and small transverse dimensions is at least about 0.003 inch (0.076 mm) and for dilatation catheters for peripheral use the differential should be at least about 0.005 inch (0.127 mm). The transverse cross-sectional dimensions of the catheter shaft may be decreased along the length of the shaft to provide a more flexible distal shaft section, but the differential requirements between the large and small transverse dimensions should still be followed. In one presently preferred embodiment the proximal catheter shaft is essentially elliptical or oval shaped in the transverse direction and the distal section slightly oviform. However, the entire length of the catheter shaft to a location proximal to the balloon may have the same oblong shape such as elliptical or oval. Further details and the advantages of an oblong transverse cross-sectional shape of the catheter shaft are found in copending application Ser. No. 08/250,708, filed on May 27, 1994, which is incorporated herein in its entirety A major advantage of the present invention is that essentially the entire catheter shaft can be extruded in a unitary fashion, thus significantly reducing the manufacturing costs thereof. The stiffening mandrel supports the proximal section which might otherwise be too flexible and provides extra pushability to the distal section with little or no loss in flexibility.

The improvements of the invention are applicable to a wide range of dilatation catheters with inflatable or expandable dilatation members on their distal extremities, such as those described in the patents incorporated herein by reference. These and other advantages of the invention will become more apparent from the following detailed description of the invention, when taken in conjunction with accompanying exemplary drawings.

BRIEF DESCRIPTION OF THE DRAWINGS

FIG. 1 is an elevational view, partially in section, of a dilatation catheter embodying features of the invention.

FIG. 2 is a transverse cross-sectional view of the catheter shown in FIG. 1 taken along the lines 2—2.

FIG. 3 is a transverse cross-sectional view of the catheter shown in FIG. 1 taken along the lines 3—3.

FIG. 4 is a transverse cross-sectional view of the catheter shown in FIG. 1 taken along the lines 4—4.

FIG. 5 is an enlarged elevation view, partially in section of the proximal extremity of the catheter shown in FIG. 1.

DETAILED DESCRIPTION OF THE INVENTION

FIGS. 1–5 schematically illustrate an over-the-wire dilatation catheter 10 embodying features of the invention. The catheter 10 includes an elongated catheter shaft 1 1 which has a proximal shaft section 12 and a distal shaft section 13 with smaller transverse and longitudinal dimensions than the proximal section, a dilatation balloon 14 mounted on the distal shaft section and a multiarm adapter 15 mounted on the proximal end of the proximal shaft section. The balloon 14 has a distal skirt 16 which is sealingly secured to the distal end of the distal shaft extension 17 which passes through the interior of the balloon. The proximal skirt 18 of the balloon 14 is secured to the exterior of distal shaft section 13. A tapered transition shaft section 19 is provided between the proximal shaft section 12 and the distal shaft section 13. The catheter shaft 11 has an inflation lumen 20 which extends from the proximal end thereof to a location in the distal shaft section 13 in communication with the interior of the balloon 14. A guidewire receiving lumen 21 is longitudinally disposed within the catheter shaft 11 parallel but off-set from the inflation lumen. It extends to the guidewire port 22 in the distal end of the distal shaft extension 17.

A stiffening or reinforcing mandrel 23 is disposed within the inflation lumen 20 having a larger dimensioned proximal section 24 and a smaller dimensioned distal section 25 with a tapered transition section 26 between the proximal and distal sections. The transition mandrel/section 26 is preferably located within the proximal shaft section 12 as indicated to provide a smooth transition between the proximal and distal shaft sections to the catheter shaft 11. A best shown in FIG. 5, the proximal end of the mandrel 23 is secured by suitable means such as an adhesive within the body 27 of the adapter 15. The mandrel 23 extends to a location just proximal to the balloon 14 and the distal tip thereof is free, i.e. unattached.

The use of the dilatation catheter shown in FIGS. 1–5 generally follows conventional PTCA practices with over-the-wire type dilatation catheters. A guidewire (not shown) is backloaded into the inner lumen 21 of the catheter shaft 11 and both the guidewire and the catheter 10 are advanced together through a guiding catheter (not shown) which has been previously disposed within the patient's arterial system. Alternatively, the guidewire may be introduced into lumen 21 through the central arm of adapter 15. The distal end of the guiding catheter is seated within the ostium of the coronary artery targeted for treatment, so that, when the dilatation catheter-guidewire assembly is advanced through the guiding catheter, the dilatation catheter exits directly into the desired coronary artery. The guidewire is usually advanced into the patient's coronary anatomy until it crosses the lesion to be dilated, and then the dilatation catheter 10 is advanced over the guidewire until the balloon 14 on the dilatation catheter is properly disposed within the stenotic region of the patient's coronary artery, so that the lesion will be dilated upon the inflation of the balloon. After the dilatation, the balloon 14 is deflated and the catheter 10 and the guidewire may then be withdrawn from the patient. If further treatment or diagnosis is to be conducted, the guidewire can be replaced with an exchange wire before removing the dilatation catheter so that the first catheter can be removed and another advanced into the desired location or an extension wire can be attached to the proximal end of the guidewire in place which extends out of the patient to perform essentially the same function. A more detailed discussion of the use of exchange wires and extension wires may be found in U.S. Pat. No. 4,827,941 (Taylor et al.) which has been incorporated herein by reference.

The various components of the catheters and guidewires of the invention can be formed from a wide variety of conventional materials. The catheter shaft may be made by extruding polymeric materials such as polyethylene, polyvinyl chloride, nylon, a polyester such a Hytrel® (which is available from DuPont), polyetheretherketone (e.g. Grade 381G from Victrex, U.S.A.) and other suitable polymeric materials. The balloon may be made from polyethylene, polyethylene terephthalate and other relatively inelastic polymers and other materials.

The dimensions of the catheter of the present invention generally follow the dimensions of conventional intravascular catheters. For coronary use the length, excluding the adapter, is typically about 135 cm and the maximum outer dimension of the catheter shaft is about 0.02 to about 0.06 inch 0.51–1.52 mm). The transverse shape of the catheter shaft may be varied. For example, in one presently preferred embodiment the proximal shaft section may have an elliptical or oval shaped transverse cross-section and the distal shaft section may have a slightly oviform shaped transverse cross-section which allows the dimensions of the inflation lumen to be reduced as the dimensions of the mandrel are reduced. In other embodiments the shape of the transverse cross-section may be the same along the length of the catheter shaft up to the balloon. The transverse dimensions of the distal shaft section may be smaller than the transverse dimensions of the proximal shaft section.

The transverse dimensions of the mandrel to a great extent depend upon the strength of the material from which the mandrel is made. Additionally, when the mandrel is disposed within the inflation lumen, the transverse dimensions of the mandrel should be chosen so as to not reduce the effective transverse cross-section of the inflation lumen which may provide excessively long inflation or deflation times. With presently preformed mandrel made of stainless steel, the proximal section typically has a diameter of about 0.01 to about 0.015 inch and the distal section a diameter of about 0.004 to about 0.009 inch. The length of the distal section of the mandrel is about 10 to about 40 cm, the transition section about 0.25 to about 10 cm and the proximal section about 80 to about 130 cm. Typical mandrel dimensions would be an overall length of 135 cm, a proximal section length of 112.5 cm, a distal section length of 22 cm and a transition section length of about 0.5 cm, with a proximal diameter of about 0.013 inch and a distal diameter of about 0.007 inch. The mandrel may be made of stainless steel, pseudoelastic nickel-titanium alloys, a high strength cobalt-nickel alloy such as MP35N which is available from Carpenter Technology Corporation and which has a nominal composition of about 35% Co, about 35% Ni, about 20% Cr and about 10% Mo and other suitable materials.

While the invention has been described herein primarily in terms of certain preferred embodiments, those skilled in the art will recognize that various modifications and improvements may be made without departing from the scope of the invention.

What is claimed is:

1. A dilatation catheter for performing an angioplasty procedure, comprising:
   a) an elongated catheter shaft having proximal and distal ends, a relatively stiff proximal catheter shaft section, a relatively flexible distal catheter shaft section that is more flexible than the relatively stiff proximal shaft section, a guidewire port in the distal end, a guidewire receiving inner lumen extending therein to the guidewire port in the distal end, an inflation lumen off-set from and parallel to the guidewire receiving inner lumen extending therein to a location spaced proximally of the distal end of the catheter shaft, and an oblong transverse cross-section along a substantial portion of its length formed of a unitary extrusion of polymer material with the inflation and guidewire receiving lumens extending through the unitary extrusion;
   b) an inflatable dilatation member mounted on the distal catheter shaft section proximal to the distal end of the catheter shaft which has an interior in fluid communication with inflation lumen, and wherein at least a portion of the guidewire receiving lumen extends through the interior of the inflatable dilatation member; and
   c) an elongated mandrel which has a relatively stiff proximal section and a relatively flexible distal section that is more flexible than the relatively stiff proximal mandrel section and which is disposed within the inflation lumen and extends within the proximal catheter shaft section and the distal catheter shaft section, with a distal tip located proximal to a distal skirt of the inflatable dilatation member and with at least a portion of the relatively flexible distal section of the mandrel within the proximal catheter shaft section.

2. The dilatation catheter of claim 1 wherein the distal mandrel section has at least one transverse dimension smaller than a corresponding transverse dimension of the proximal mandrel section.

3. The dilatation catheter of claim 1 wherein the longitudinal location of the mandrel within the inflation lumen in the catheter shaft is fixed.

4. The dilatation catheter of claim 3 wherein the catheter has an adapter mounted on the proximal end of the catheter shaft and the mandrel has a proximal end secured within the adapter to fix the longitudinal location of the mandrel within the inflation lumen.

5. The dilatation catheter of claim 1 wherein the distal mandrel section is about 10 to 40 cm in length.

6. The dilatation catheter of claim 1 wherein the distal catheter shaft section has at least one transverse dimension which is smaller than a corresponding transverse dimension of the proximal catheter shaft section.

7. The dilatation catheter of claim 1 wherein the distal catheter shaft section proximal to the inflatable dilatation member is about 10 to about 40 cm in length.

8. The dilatation catheter claim 1 wherein the proximal section of the mandrel is longer than the distal section thereof.

9. The dilatation catheter of claim 8 wherein the mandrel has a tapered section between the proximal and distal sections to provide a smooth transition therebetween.

10. The dilatation catheter of claim 9 wherein the proximal section of the mandrel is sufficiently shorter than the proximal section of the catheter shaft so that the transition section of the mandrel is located within the proximal section of the catheter shaft.

11. The dilatation catheter of claim 1 wherein the oblong transverse cross-section of the catheter shaft has a large transverse dimension and a small transverse dimension perpendicular to the large transverse dimension, with the large transverse dimension being about 1.1 to about 3 times the small transverse dimension.

12. The dilatation catheter of claim 1 wherein the distal section of the catheter shaft has an oviform transverse cross-sectional shape.

13. The dilation catheter of claim 1 wherein the proximal section of the catheter shaft has an elliptical transverse cross-sectional shape.

14. The dilatation catheter of claim 1 wherein the proximal section of the catheter shaft has an oval transverse cross-sectional shape.

15. A dilatation catheter for performing an angioplasty procedure, comprising:
   a) an elongated catheter shaft having proximal and distal ends, a relatively stiff proximal catheter shaft section, a relatively flexible distal catheter shaft section that is more flexible than the relatively stiff proximal shaft section and that has at least one transverse dimension which is smaller than a corresponding transverse dimension of the proximal catheter shaft section, a guidewire port in the distal end, a guidewire receiving inner lumen extending therein to the guidewire port in the distal end, an inflation lumen off-set from and parallel to the guidewire receiving inner lumen extending therein to a location spaced proximally of the distal end of the catheter shaft, and an oblong transverse cross-section along a substantial portion of its length formed of a unitary extrusion of polymer material with the inflation and guidewire receiving lumens extending through the unitary extrusion;
   b) an inflatable dilatation member mounted on the distal catheter shaft section proximal to the distal end of the catheter shaft which has an interior in fluid communication with inflation lumen, and wherein at least a portion of the guidewire receiving lumen extends through the interior of the inflatable dilatation member; and c) an elongated mandrel which has a relatively stiff proximal section and a relatively flexible distal section that is more flexible than the relatively stiff proximal mandrel section and which is disposed within the inflation lumen and extends within the proximal catheter shaft section and the distal catheter shaft section, with a distal tip located proximal to a distal skirt of the inflatable dilatation member and with at least a portion of the relatively flexible distal section of the mandrel within the proximal catheter shaft section.

* * * * *